United States Patent [19]

Bowers

[11] 4,124,803

[45] Nov. 7, 1978

[54] SURFACE FINISH MONITOR

[76] Inventor: Kenneth Bowers, 1251 Picasso Dr., Sunnyvale, Calif. 94087

[21] Appl. No.: 753,193

[22] Filed: Dec. 22, 1976

[51] Int. Cl.$^2$ ............................................. G01N 21/48
[52] U.S. Cl. .................................. 250/559; 250/572; 356/369; 356/430; 356/448
[58] Field of Search ................ 250/559, 572; 356/118, 356/200, 212

[56] References Cited

U.S. PATENT DOCUMENTS

| | | | |
|---|---|---|---|
| 3,636,361 | 1/1972 | Bowers | 356/212 X |
| 3,734,624 | 5/1973 | Cornelius | 356/200 X |

FOREIGN PATENT DOCUMENTS 1,080,432  12/1954  France ...................................... 356/118

Primary Examiner—James B. Mullins

[57] ABSTRACT

The purpose of this invention is to reveal the surface properties, such as smoothness and resulting printability of a rapidly moving strip of material, such as paper. To accomplish this, the production process is continuously monitored, without error due to environmental conditions such as dust and dirt on optical surfaces, temperature affects, lamp degradation, etc. An index of printability relative to smoothness is obtained by integrating the plateau areas in the optical field of view. A unique combination of approach angle, selected wave length of infra red radiation, horizontal polarization of search beam, and use of four optical paths to obtain mathematical model equivalency, is employed.

3 Claims, 4 Drawing Figures

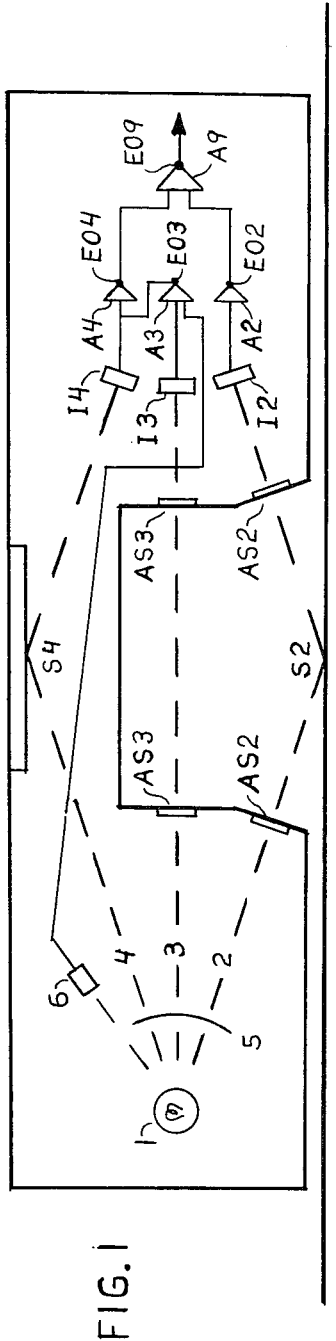
FIG. 1
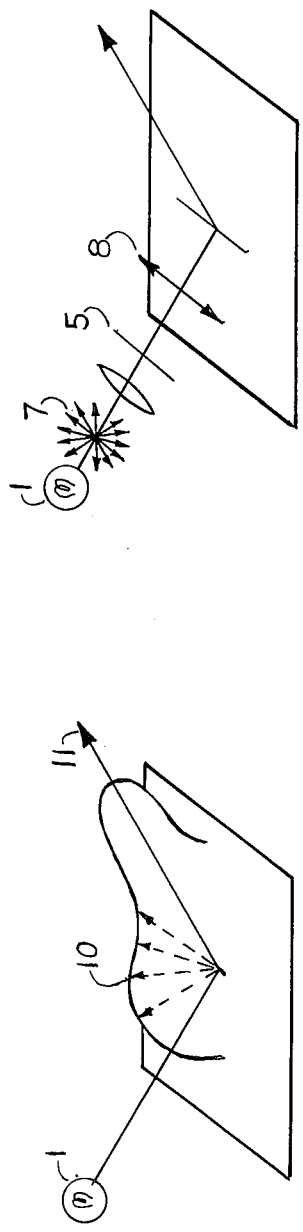
FIG. 2
FIG. 3
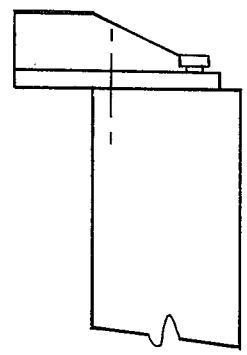
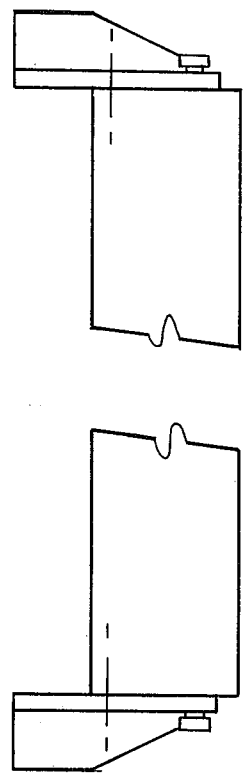
FIG. 4

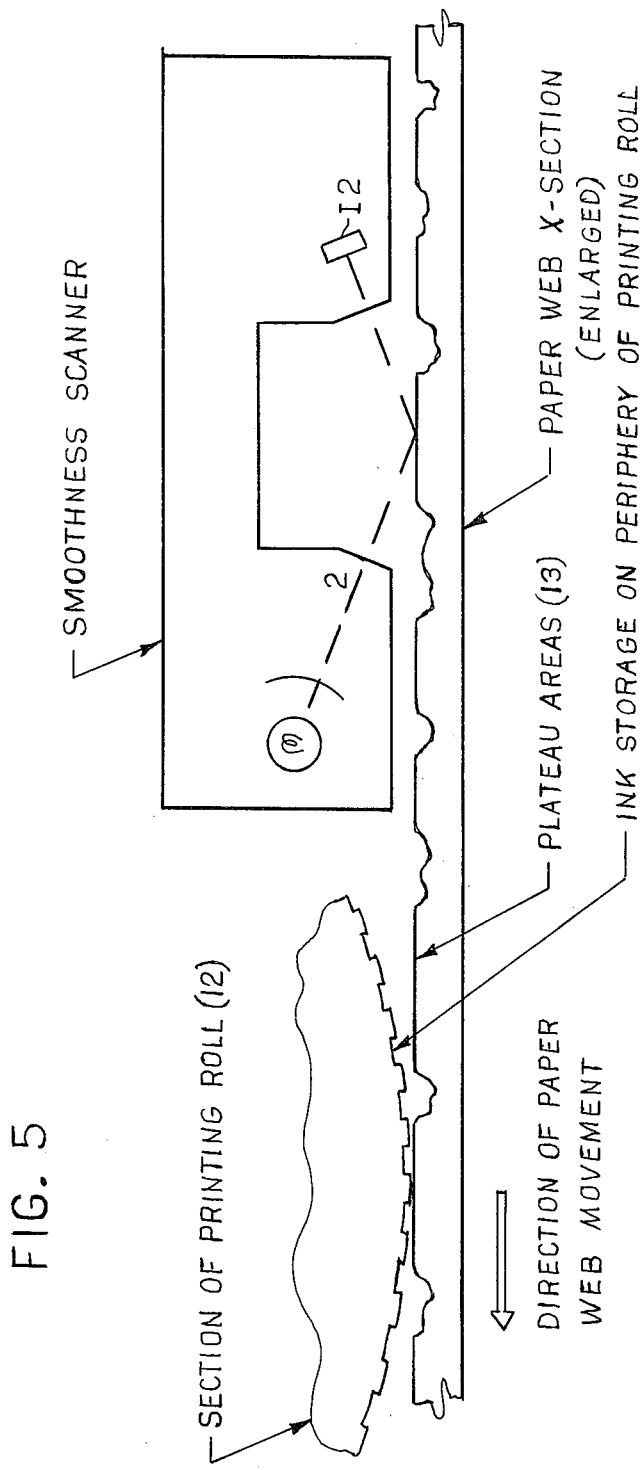

SURFACE FINISH MONITOR

BACKGROUND OF THE INVENTION

1. Field of the Invention

This invention relates to surface finish smoothness measurements and in particular to apparatus for continuously measuring the smoothness of a moving sheet or web of material and comparing the resulting smoothness measurements to a reference standard, with means to automatically compensate for environmental conditions and contaminants. 2. Prior Art In papermaking, smoothness is the characteristic of the paper's surface which is primarily responsible for the paper's capability to produce, among other uses, the uniformity of print density of a solid or full tone print, when the paper or plastic sheet is used in newsprint, periodicals, catalogs, flexible packaging displays, etc.

Numerous methods have been proposed and used for surface finish measurements of smoothness, mostly laboratory methods based on the air leak principle. The instruments presently used are not adaptable for continuous on-machine monitoring for various reasons, principally because of the slow response of an air column, non-linear readout, and other restrictions which limit the method to laboratory sampling techniques.

SUMMARY OF THE INVENTION

This invention, on the other hand, overcomes these problems of the prior art smoothness measuring systems. The structure of this solution is physically adaptable to continuous on-machine monitoring, with high accuracy, fast response, and minimal maintenance.

The structure incorporates means to automatically compensate for dust and dirt, temperature changes, external light conditions, power supply voltage variations. The structure is ruggedly constructed to withstand physical stresses, and at the same time permit accurate calibration and cleaning without removing the structure from the paper machine.

Prior art optical systems using visible light based on reflectance principles, have not been adaptable for measuring surface characteristics only because part of the light energy is absorbed into the material. This invention incorporates means to eliminate the error due to the absorbed energy, and provide for a surface-only measure of smoothness.

BRIEF DESCRIPTION OF THE DRAWINGS

FIG. 1 shows the surface finish smoothness sensing unit of the invention;

FIGS. 2 and 3 show the reflection of unpolarized radiation and horizontally polarized radiation, respectively;

FIG. 4 shows another embodiment of the invention; and

FIG. 5 shows an application of the invention.

DETAILED DESCRIPTION

FIG. 1 shows the surface finish smoothness sensing unit, or scanner, of this invention, including the differential comparator/computer. The scanning unit is positioned as shown, relative to the sheet or web of material being measured.

FIG. 1 shows the optical paths 2, 3, 4, and 6, with appropriate windows and optics, silicon sensors and solid state amplifiers used in the computer system. The source of radiant energy is a long life incandescent lamp 1 with suitable infra-red filters in all optical paths to provide a source of infra-red radiation of a selected wavelength which permits maximum response of the photo sensors. This allows the lamp to be operated at reduced voltage for long life and maximum efficiency. Also included in the optical paths with the infra-red filters is a polarizer labeled 5 in FIG. 1. The purpose of the polarizer is to horizontally polarize the incident beam in paths 2 and 4 so that all the radiant energy of the incident beam is reflected off the surface of the material being measured and the standard, and none of this energy is absorbed.

This invention provides a solution to the problem of measuring surface characteristics only. As briefly mentioned in the Summary, prior art optical systems using visible light based on reflectance principles, have not been adaptable for surface measurements. This is because part of the radiant energy is absorbed into the material (See FIG. 2) and part of the energy leaves the material as scattered or diffused light 10. The percentage of this scattered and absorbed energy relative to the total impinging light beam energy varies depending upon the matrix of the material into which the radiation energy penetrates and the color mix of the particles below the surface of the material. The remaining portion of the impinging radiation is specularily reflected 11 and is commonly used to measure specular gloss. However, there is always the uncertain variable of the scattered light which varies with the mix of material. According to this invention, this variable factor is eliminated by means of:

(a) Using infra-red radiation in place of visible light. According to text book theory, the degree of penetration of a radiation beam into a material is dependent upon the wavelength of the radiation, with infra-red having minimal penetration compared to visible light because infra-red has a lower wavelength.

(b) Horizontally polarizing the impinging infra-red beam with a polarizer, insures that all the incident radiation energy is reflected and none is absorbed.

Polarizer 5 shown in FIG. 1 is the conventional type. The purpose is to cut off the vertical component of the radiation field 7 as shown in FIG. 3. Therefore, when the horizontally polarized radiation beam 8 strikes at an oblique angle to the measured surface, that portion of the radiation field which, in the unpolarized state would strike the paper surface first, is removed by the polarization process. The normal unpolarized beam would have penetrated into the material and cause scattered radiation. The measurement would not then be a true surface indication.

Using the means herein described to measure smoothness as it relates to the printability of paper, it is apparent that this invention has the capability to give an integrated value of all the flat, plateau areas in the optically covered field of view of the instrument described by this invention. For FIG. 5, optical beam 2 is surface reflected off the plateau areas 13 of the paper web, and is picked up by sensor i-2. The scattered radiation which bounce off the slopes of the paaper web cannot reach sensor i-2. Therefore, the intensity of the reflection from the plateau areas is directly related to the area and number of these plateaus in the optically covered area. The electrical output of sensor i-2 provides an integrated reading of the total area of all the plateaus in the optically covered area. In the printing process, these are the areas where ink is transferred to the printed surface by the print roll or plate 12. Therefore, the integrated smoothness measurement is a function of ink distribution over the printed area, and is therefore, an indicator of the print quality of the paper.

FIG. 1 shows four optical paths and the associated electronic circuitry comprising the computer system by which a measurement of surface finish smoothness only is obtained with this invention. The means by which the attenuation effects due to dust and dirt accumulations on the window surfaces of optical path 2 are balanced out, are described herein.

Referring to FIG. 1, infra-red sensor 6 which is contained in the lamp compartment, senses only the output of the lamp source. This sensor output is balanced out in amplifier A-3 by the sensor output $i$-3 of optical path 3, so that the voltage output $eo$-3 of amplifier A-3 contains only a negative voltage component. This voltage component is impressed upon the input of amplifier A-4 as a proportional current flow which is algebraically added to the sensor current $i$-4 of optical path 4. The voltage output of amplifier A-4 now contains not only the signal representing the smoothness of the standard, but also a component representing the attenuation effects of dust and dirt $\Delta s$-3. The attenuation $\Delta s$-3 is equal to the attenuation $\Delta s$-2 in optical path 2 because the windows of optical path 3 are identical to, and contiguous to, those of optical path 2. Since amplifiers A-2 and A-4 now have an equal component representing dust and dirt in optical paths 2 and 4, when these amplifier outputs, $eo$-2 and $eo$-4 are impressed upon the input of amplifier A-9, these components cancel out. Now when voltage signal $eo$-2 representing the smoothness measurement of optical path 2, is electrically compared with voltage signal $eo$-4 representing the smoothness measurement of optical path 4, the voltage output $eo$-9 of the differential amplifier A-9, provides a true measure of the difference in smoothness between the production material and the standard.

The electrical output $eo$-3 also operates an electronic relay which gives a warning signal when lamp 1 is burned out. A mathematical model of the circuitry described and shown on FIG. 1 is derived as follows:

$$eo9 = eo4 - eo2$$

$$eo9 = (1 - S4) - [1 + (1 - \Delta S3)] - (1 - \Delta S2 - S2)$$

$$eo9 = -S4 - 1 + 1 - \Delta S3 - 1 + \Delta S2 + S2$$

$$eo9 = S4 + S2$$

$$eo9 = 0 \text{ When: } \Delta S3 = \Delta S2 \text{ And } S4 \ 32 \ S2$$

Referring to FIG. 1, the collimating lenses in beams 4, 3 and 2 collimate the infra-red energy from common source 1 and project beams onto the material being measured, the standard or master, and through the environment (beam 3). Another one of the unique features of this invention is the means used to build a tolerance into the system so that the spacing distance between the scanner structure and the surface of the material being measured, can tolerate a variation in spacing distance. This distance is a very critical factor because of the geometry of optical beam 2 with respect to the material surface. Because of this critical spacing factor, contemporary instruments of this kind have experienced difficulty in applying such critical geometry to on-machine measurements. This invention makes possible the practical use of such critical optical geometry.

The means used in this invention is to make collimating lens in beam 2 slightly larger in diameter to insure that the reflected beam will always cover the sensor area even when the material surface varies from the normal spacing distance within the design tolerance.

There is also a means used in this invention of maintaining the aforementioned critical spacing distance when it is necessary to move the scanner structure away from the measured surface for cleaning and calibration. This method is the use of a swivel bracket arrangement shown in FIG. 4 which allows moving the scanner away from the measured surface without removing the structure and detaching it from the paper machine. After cleaning and calibration, the scanner can be placed in exactly the same position relative to the paper surface as it was before the cleaning and calibration operation. This insures a high degree of maintainability and accuracy of this instrument.

What is claimed is:

1. Structure comprising:
    a radiant energy source;
    a first sensing means:
    first path means for transmitting radiant energy from said source to the surface of a material, and for transmitting radiant energy reflected from said surface to said first sensing means, said first sensing means producing a first intermediate signal representing the radiant energy from said source reflected by said surface;
    a second sensing means;
    second path means for transmitting radiant energy from said source through substantially the same environment passed through by the radiant energy transmitted by said first path means to said second sensing means, said second sensing means producing a second intermediate signal representing the radiant energy transmitted through said second path means.
    a third sensing means;
    third path means for transmitting radiant energy from said source to the surface of a reference standard, and for transmitting the radiant energy reflected by said reference standard to said third sensing means, said third sensing means producing a third intermediate signal representing the radiant energy reflected by said reference standard;
    a fourth sensing means;
    fourth path means for transmitting radiant energy from said source to fourth sensing means, said fourth sensing means producing a fourth intermediate signal representing the radiant energy of the said radiant energy source only;
    means for processing said first, second, third and fourth intermediate signals to provide a measure of the radiant energy reflected by said surface of a material, said measure being independent of environmental contaminants which interfere with the radiant energy transmitted through said first path means; also independent of degradation of said radiant energy source.

2. Structure as in claim 1 in which said means for processing comprises:
    a first amplifier means for receiving first intermediate signal;
    a second amplifier means for receiving second intermediate signal, and fourth intermediate signal, and for producing an output signal which represents the difference between the second intermediate signal and the fourth intermediate signal, the output signal of said second amplifier represents the difference caused by dust and dirt in second path means;

a third amplifier for receiving the third intermediate signal and the output siganl of said second amplifier, the output signal of said third amplifier represents the third intermediate signal minus the compensating signal of said second amplifier;

a fourth amplifier for receiving the output of said first amplifier and the output of said third amplifier, the output signal of said fourth amplifier represents the difference between the first intermediate signal and the third intermediate signal adjusted for dust and dirt collection on optical surfaces.

3. Structure as in claim 1 in which said first path means and said third path means are at a grazing incidence of approach angle to the reflecting surfaces.

* * * * *